United States Patent [19]

Fournier

[11] 4,402,939

[45] Sep. 6, 1983

[54] VACCINATING GLYCOPEPTIDIC ANTIGENIC FRACTION WITH A VERY HIGH LEVEL OF IMMUNOGENICITY, ISOLATED FROM CULTURES OF PATHOGENIC GERMS, PROCESSES FOR ISOLATING SAID FRACTION AND VACCINES CONTAINING SAID FRACTION

[75] Inventor: Jean-Michel Fournier, Paris, France

[73] Assignee: Institut Pasteur, Paris, France

[21] Appl. No.: 163,076

[22] Filed: Jun. 26, 1980

[30] Foreign Application Priority Data

Jun. 29, 1979 [FR] France .................. 79 16851

[51] Int. Cl.³ ............... A61K 39/02; A61K 37/02
[52] U.S. Cl. .................... 424/92; 424/177; 424/180; 424/88
[58] Field of Search .................. 424/88–92, 424/12, 177

[56] References Cited

U.S. PATENT DOCUMENTS

| | | | |
|---|---|---|---|
| 3,342,684 | 9/1967 | Lembke et al. | 424/92 |
| 3,395,219 | 7/1968 | Millman | 424/92 |
| 3,855,197 | 12/1974 | Hirsch et al. | 260/112 R |
| 3,929,994 | 12/1975 | Hirsch et al. | 424/177 |
| 4,010,257 | 3/1977 | Adlam et al. | 424/92 |
| 4,069,314 | 1/1978 | Adlam et al. | 424/92 |
| 4,123,520 | 11/1978 | Hagopian et al. | 424/92 |
| 4,203,970 | 5/1980 | Carlo et al. | 424/92 |

FOREIGN PATENT DOCUMENTS

| | | |
|---|---|---|
| 2171909 | 9/1973 | France . |
| 2253499 | 12/1973 | France . |
| 2215945 | 8/1974 | France . |
| 1489896 | 10/1977 | United Kingdom . |

OTHER PUBLICATIONS

Chemical Abstracts, vol. 74, p. 255, Abst. No. 85782g, 1971.
Nogel, J., "Isolation from Bordetella Pertussis of Proctective Additive Free from Toxic Activity and Histomine Sensitizing Factor", *Nature*, vol. 214, Apr. 1, 1967, pp. 96–97.
Van Hemert, P., "Preparation of Soluble Pertussis Vaccine", *Nature*, vol. 203, Aug. 15, 1964, 774–775.
*Chemical Abstracts*, vol. 69, No. 21, Ref. 85020d, p. 7940, 11/19/68 of Pasztai, Z, *Ann. Immunol. Hung*, 1967, 10.55–62.
*Microbiology Abstracts*, vol. 6, No. 5, Feb. 1971, Section B, Ref. B3786 of Orr et al., *Infect. Immunity*, 2, 543–548 (1970).
Chemical Abstracts, vol. 67, p. 160, Abst. No. 1776c, 1967.
Chemical Asbtracts, vol. 58, Abst. No. 14577c, 1963.

*Primary Examiner*—Blondel Hazel
*Attorney, Agent, or Firm*—Browdy & Neimark

[57] ABSTRACT

A glycopeptic vaccinating antigenic fraction with a very high level of immunogenicity, which is isolated from a culture of pathogenic germs comprises an osidic part present in a proportion of about 50%, with a proteinic part, which are linked together by covalent bond; when it is opposed to a suitable immune-serum, the fraction has an immunological image which essentially comprises a 'clear' line of precipitation close to the antigen pit, in immunodiffusion in gelose. The fraction is used for the preparation of vaccines and as a diagnostic agent.

17 Claims, 3 Drawing Figures

VACCINATING GLYCOPEPTIDIC ANTIGENIC FRACTION WITH A VERY HIGH LEVEL OF IMMUNOGENICITY, ISOLATED FROM CULTURES OF PATHOGENIC GERMS, PROCESSES FOR ISOLATING SAID FRACTION AND VACCINES CONTAINING SAID FRACTION

The present invention relates to a glycopeptidic vaccinating antigenic fraction, with a very high level of immunogenicity, which is isolated from cultures of pathogenic germs, and to processes for the extraction of said antigenic fraction from cultures of pathogenic germs and for purification in order to isolate the glycopeptidic active constituent; the invention also relates to the preparation of vaccines with a very high level of immunogenicity, containing said fraction.

BACKGROUND OF THE INVENTION

There are many medical uses at the present time for antigenic fractions: serotherapies of all kinds, serodiagnosis, detection of pathogenic germs in the widest range of pathological substances, epidemiological investigations and in particular vaccinations. As is known, vaccination is often the only weapon and the only prophylaxis which is available against many illnesses, hence the importance afforded by researchers to the development of processes for producing antigens which have a high level of antigenicity and a high degree of specificity. Research has first been directed towards producing an immunization effect with regard to bacterial infections, in particular enteric infections, which are induced for example by bacteria of the group of Salmonella and more particularly Salmonella thyphimurium, by means of a vaccine comprising entire killed bacteria. However, the use of such vaccines is not entirely without danger because of their toxicity due to the substantial endotoxin content in the cellular membrane of said bacteria, which toxicity is the cause of allergic reactions which are sometimes very serious. Attempts have therefore been made to prepare vaccines which comprise purified fractions extracted from bacterial cultures. Thus, there have been proposed vaccines which are produced from surface antigenic fractions extracted from Brucella melitensis and Brucella abortus, which essentially comprise a lipopolysaccharide-protein complex (cf DIAZ, JONES, LEONG and WILSON, Journal of Bacteriology, October 1968, volume 96, No. 4, pages 893–901, 'Surface antigens of smooth Brucellae'). It should be noted that the writers of the above-quoted Article report that, if the active constituent of the antigenic fraction is the above-mentioned lipopolysaccharide-protein complex, the antigenic fraction nonetheless also contains proteinic components associated with internal Brucellae antigens, and a polysaccharide-protein complex which is without any lipid, of which it is said that it would apparently not play an important part in agglutination reactions because its antibodies could be separated by absorption without affecting the rate of agglutination. Likewise, there have been proposed vaccines which are polyvalent against Pseudomonas aeruginosa, which are produced from surface antigens having a high level of immunogenicity and which essentially comprise a highly immunogenic lipopolysaccharide-protein complex which is without toxic constituents, extracted from cultures of bacteria on a special medium.

Another proposed solution for eliminating the toxicity due to the endotoxin of the membranes of the cells of the bacteria is represented by acellular vaccines which, as the source of antigens, use the excretion products (or 'slime') of bacterial cultures, in particular cultures of Pseudomonas aeruginosa, which have previously been freed, by a washing operation, of the toxic products which are also contained in the slime, in particular labile excretion products and impurities from the culture medium (see French Pat. No. 2 290 219 of Nov. 5th 1974 to INSTITUT PASTEUR and P BERCHE, M VERON and R TINELLI, Ann. Microbiol. (Institut Pasteur) 1976, 127A, pages 247-259).

However, these various attempts at purifying bacterial cultures have not achieved their aim in that on the one hand they have not made it possible effectively to identify the antigenic constituent capable of giving the desired immunization effect and on the other hand they have not made it possible to produce vaccines which are effectively without toxicity. Research has therefore been continued in these two directions. Thus, there has been proposed an antigenic fraction which is extracted by suitable processes from cultures of pathogenic germs, in particular cultures of Salmonella thyphimurium, Malleomyces mallei, Pseudomonas mallei, and Vibrio cholerae, which would not have the allergic reactions of the previously proposed vaccines; this antigenic fraction which was identified as being a lipidoproteinic fraction is characterized in that it corresponds to the first peak on the diagram of absorption in ultraviolet at 280 nm, and that, when opposed to an immuneserum produced in an animal from the same culture, it gives the band (or the pair of bands) which is closest to the antigen well in the test of diffusion in a gelose medium and in the immunoelectrophoretic analysis test (see French Pat. No. 73 03734 of 2nd February 1973 to ANVAR, inventor: A DODIN). It has been found however that none of the attempts at immunization by the proposed purified antigenic fractions was satisfactory, because those fractions all contain a lipidic portion to which it was possible to attribute toxicity (see Lü DERITZ, GALANOS, LEHMANN, NURMINEN, RIETSCHEL, ROSENFELDER, SIMON and WESTPHAL, 1973, 'Lipid A: Chemical structure and biological activity' in 'Bacterial lipopolysaccharides', edited by KALL and WOLFF, the University of Chicago Press, Chicago). Although experiments were carried out in order to obtain immunization in mice with respect to Pseudomonas aeruginosa, by capsular polysaccharides extracted from Pseudomonas aeruginosa slime (see PIER, SIDBERRY & SADOFF, INFECTION and IMMUNITY, December 1978, volume 22, No. 3, pages 908–918 and PIER et alia, loc. cit. pages 919–925), it is nonetheless admitted that it is not possible to prepare vaccines from polysaccharides, whether they are extracted from the excretion products of bacterial cultures or produced by cutting the lipidic portion of the lipopolysaccharides (LPS) molecule, considering that such vaccines have a very low level of immunogenicity which is because the polysaccharides, both those which are capsular and those which are produced from the slime, if being responsible for antigenic specificity, are devoid of immunogenicity.

It has also been proposed that mice should be immunized with regard to Bordetella pertussis, by means of an oligopeptide isolated from that bacterium, from a group of ribonucleoproteins of low molecular weight (see WILHELM & ROMER, zbl. Bakt. Hyg., I Abt., Orig. B 166, pages 264-271 (1978)), immunisation by peptidic complexes of organisms containing deoxyribonucleic acids, which complexes are presented as having specific antigenic properties with regard to the organism from which they are isolated, also being proposed by French Pat. No. 2 387 991 of 19th April 1978 to R. and Z. VERMÖ GENSVERWALTUNGS-GESELLSCHAFT GmbH.

However, prior to the latter publications, the proteins associated with the endotoxin present in the cellular membrane of the bacteria were considered as ,dditives suited to stimulating the production of antibodies and not as having an antigenic activity in themselves (see AMSTEDT & LINDHOLM, Immunology, 33, pages 629–633 (1977)). Likewise, a certain number of patents have been filed for vaccines in which the polysaccharides and/or the glycopeptides are included as immunity and stabilization additives associated with ARN or the ribosomes extracted from pathogenic germs.

Another direction in which research has been carried on consisted of preparing a synthetic polysaccharide-protein conjugation product which can be used as an active immunogen with regard to different pathogenic germs (in particular Pneumococci, Salmonella), starting from the consideration that the polysaccharide portion of the membrane lipopolysaccharide (LPS) of the bacteria enjoys antigenic specificity whose importance is primordial with regard to the immunogenicity of the vaccine, and that, if that polysaccharide could be linked as haptene constituting an excellent antigenic determinant, to a carrier formed by an immunogenic protein without toxicity, the result which would be achieved is an immunogenic agent for the preparation of specific vaccines (see PAUL, KATZ and BENACERAF, The Journal of Immunology, volume 107, No. 3, September 1971, pages 658–688; EKBORG et alia, Immunochemistry (1977), volume 14, pages 153–157; SVENSON and LINDBERG, FEMS Microbiology Letters 1 (1977), pages 145–148; LINDBERG et alia, INFECTION & IMMUNITY, volume 10, No. 3, September 1974, pages 541–545; SVENSON and LINDBERG, The Journal of Immunology, volume 120, No. 5, May 1978, pages 1750–1757; ZOPF et alia, Archives of Biochemistry and Biophysics, volume 185, No. 1 (1978), pages 61–71; SVENUNGSSON and LINDBERG, Acta Path. Microbiol. Scand. Sect. B,86, pages 35–40 (1978)). However, the comparative tests carried out by the different researchers have shown that, if such synthetic conjugation products may indeed have immunogenic activity and the absence of toxicity which was expected thereof, their immunogenic activity is nonetheless very much lower than that of the vaccines produced from entire dead bacteria.

GENERAL DESCRIPTION OF THE INVENTION

The aim of the present invention is consequently to provide for a vaccinating antigenic fraction with a very high degree of immunogenicity, which is isolated from cultures of pathogenic germs, which has a given glycopeptidic composition, and which is characterized by a clearly defined immunological image.

The present invention concerns a vaccinating antigenic fraction with a very high level of immunogenicity and which is isolated from a culture of pathogenic germs, characterized in that is comprises an osidic part present in a proportion of about 50% with a proteinic part, which are linked together by colvalent bond, and that, when it is opposed to an imune-serum from an animal treated by the same culture, the fraction has an immunological image which essentially comprises a 'clear' line of precipitation close to the well of the antigen, in immunodiffusion in gelose.

In accordance with an advantageous embodiment of said vaccinating antigenic fraction, the fraction is characterized in that is has, in immunodiffusion in gelose, in addition to the above-mentioned 'clear' line of precipitation which is close to the well of the antigen, in which the presence of amino acids has been shown by marking with iodine 125 with chloramine T, a 'blurred' line of precipitation which is in a position variable between the wells of antigen and antibodies, and which reveals the participation of polyosides in the formation of this second precipitate.

In accordance with an advantageous characteristic of the vaccinating antigenic fraction according to the present invention, said fraction is distinguished in that the immunological image as a 'clear' line obtained in immunodiffusion in gelose is not modified after treatment of the vaccinating antigenic fraction according to the invention, by proteases.

In accordance with another advantageous feature of the vaccinating antigenic fraction according to the present invention, said fraction is distinguished in that its immunological image of a 'clear' line obtained in immunodiffusion in gelose disappears after treatment of said fraction with sodium hydroxide.

Also in accordance with the invention, the vaccinating antigenic fraction is distinguished in that the appearance of the 'blurred' precipitation line is inhibited, in immunodiffission in gelose, if oses or monosaccharides are added to the gelose in which the immunodiffusion reaction is produced.

This inhibition reveals the partaking of polyosides in the formation of the second precipitate, defined immunochemically by a 'blurred' line.

According to the invention, it has been shown that the presence of the determinants responsible for the formation of the 'clear' line precipitate is essential for the antigenic fraction according to the invention to give good protection, by the following experiments:

capsular polyoside extracted from Klebsiella pneumoniae gives, in immunodiffusion, only little precipitate with a 'clear' line and, in contrast, a great deal of 'blurred' line precipitate; its protective ability on mice is very low (of the order of 80 ng);

preparations of surface antigens which, in immunodiffusion, give only the 'clear' line precipitate, are highly active in the protection test (1 ng);

the treatment with sodium hydroxide of surface antigen preparations, which causes the 'clear' line precipitate to disappear, considerably reduces the protective ability of the preparation (at least by a factor of 100).

In accordance with an advantageous embodiment of the vaccinating antigenic fraction according to the invention, the fraction is isolated from cultures of pathogenic germs which neither secrete or excrete toxins and which contain a protective antigen defined by a line of precipitation which is centered on the antigen well, in immunodiffusion in gelose, when it is opposed to an immune-serum from an animal treated by a culture of the same pathogenic germ.

In accordance with an advantageous mode of carrying this embodiment into effect, the vaccinating antigenic fraction is isolated from cultures of pathogenic germs selected from the group which comprises Klebsiella pneumoniae, Streptococcus pneumoniae, Pseudomonas aeruginosa, Vibrio cholerae, Hemophilus influenze, and Bordetella pertussis.

In accordance with an advantageous feature of the vaccinating antigenic fraction according to the present invention, said fraction is distinguished in that the peak produced by column chromatography corresponds (for an absorption at 280 nm in ultra-violet) to a composition of the order of 25 to 25.55% of proteins and of the order of 73.40 to 73.42% of capsular polysaccharides, the phosphorus content not exceeding approximately 0.41%, the proportion of 2-keto-3-deoxyoctanoate (KDO) specific of the LPS being less than 0.32% and the proportion of N-acetylglucosamine being less than 0.32%.

Such analysis reveals on the one hand the glycoproteinic composition of the vaccinating antigenic fraction according to the invention, and, on the other hand, the absence of ADN or ARN.

The present invention also concerns processes for the extraction and purification of surface antigens of cultures of pathogenic germs, to produce the vaccinating antigenic fraction with a high degree of immunogenicity, as defined hereinbefore.

In accordance with a process for extracting and purifying surface antigens from a culture of pathogenic germs, in accordance with the invention, the bacterial deposit is extracted one to several times, with very vigorous agitation, by a suitable buffer with a pH-value of close to 6, the supernatant obtained containing the crude surface constituents is concentrated by ultra-filtration, collecting only particles whose molecular weight is higher than 10 000, the ultra-filtrate produced is treated with sodium deoxycholate (DOC) in a suitable buffer with a pH-value of close to 8, the treated ultra-filtrate is precipitated from absolute ethanol, the resulting precipitate is dissolved with the same buffer with a pH-value of close to 8, with the addition of 2% of DOC, it is then dialyzed against the buffer tris-HCl, pH-value 8, adsorbed on DEAE-cellulose, the antigen is eluted with the same buffer used with increasing molarity, and then concentrated by ultra-filtration.

In accordance with an advantageous embodiment of the process of the present invention, the bacterial deposit is extracted by a buffer comprising:

| lithium acetate | 0.2 M |
|---|---|
| EDTA | 10 mM |
| sodium azide | 0.02% |
| acetic acid QSP → | pH-value 6 | in a ratio of 50 to 70 ml of the buffer per g of wet bacterial deposit.

According to another embodiment of the process of the present invention, the solution of crude surface constituents is filtered over a millipore filter before carrying out the ultra-filtration step.

In accordance with another embodiment of the process of the invention, the ultra-filtrate which is adjusted to a pH-value of close to 8 by the buffer TRIS is treated by a 5% solution of DOC in the buffer TRIS-HCl with a pH-value of 8, comprising:

| TRIS-HCl | 10 mM |
|---|---|
| EDTA | 10 mM | so as to adjust the concentration of the solution of surface constituents to about 1% (weight/volume) of DOC.

In accordance with another embodiment of the present invention, the treated ultra-filtrate is precipitated by 4 to 5 times its volume of absolute alcohol.

In accordance with another embodiment of the invention, calibration of the tubes containing the antigen after passing over a column of DEAE-cellulose is effected by the protection test and/or the immunodiffusion test and/or the immunoelectrophoresis test.

In accordance with another process for the extraction and purification of surface antigens from a culture of pathogenic germs, in accordance with the invention, a pure vaccinating antigenic fraction as defined hereinbefore is produced by purification of a preparation containing said surface antigens by affinity chromatography.

In accordance with an advantageous embodiment of such a process, purification by affinity chromatography is carried out by using an immunoadsorbent formed by specific antibodies of the component which constitutes the 'clear' line precipitate, which are rendered insoluble by any suitable means.

In accordance with a preferred arrangement of this embodiment, said antibodies are produced by hyperimmunization of mammals such as a rabbit in particular, by a preparation of surface antigens of pathogenic germs, in respect of which immunization is to be achieved.

In accordance with a preferred method of producing said specific antibodies, they are produced by using as antigens, preparations of surface antigens which are purified by per se known biochemical methods, and which are injected into the animal to be immunized.

In accordance with another preferred method of producing said specific antibodies, they are produced by directly using the 'clear' line precipitate which is formed in the gelose in the course of the immunodiffusion reaction, which precipitate is recovered by being cut out in situ in the gelose, advantageously after washing said gelose in order to eliminate the antigens or the antibodies which are not complexed in the course of the immunodiffusion reaction, whereafter it is injected into the animal to be immunized.

In accordance with this method of producing the specific antibodies, the 'clear' line precipitate is produced by using specific purified reactants of the determinant; or else it is produced by using preparations of antigens and antibodies which are not purified.

In accordance with this process of extracting and purifying surface antigens, the specific antibodies used as immuno-adsorbents in the method of purifying the antigens by affinity chromatography are recovered in the usual way after having collected the blood of the hyperimmunized animals and after having separated from the red blood corpuscles, the serum which is rich in specific antibodies.

In accordance with a preferred form of this process, the specific antibodies which are recovered in this way are rendered insoluble by polymerization by means of glutaraldehyde or by fixing on beads of gel of dextran, Sepharose or glass, for example, which are activated by cyanogen bromide or similar.

In accordance with another preferred form of this process, the preparation of surface antigens, which is subjected to purification by affinity chromatography, comprises a culture of bacteria or by the supernatant of such a culture, or by the supernatant which contains the crude surface constituents and which is produced by extraction of a bacterial deposit, or by the ultra-filtrate which is obtained after ultra-filtration of the supernatant containing the crude surface constituents and treatment of the said supernatant by sodium deoxycholate (DOC).

The present invention also concerns the use of the vaccinating glycopeptidic antigenic fraction with a very high level of immunogenicity, in accordance with the present invention, for the preparation of vaccines, and as a diagnostic agent.

In addition, the present invention also concerns the use of the specific antibodies produced by hyperimmunization of suitable animals, by means of the glycopeptidic vaccinating antigenic fraction according to the present invention, as reagents for characterizing the protective antigen, in particular by precipitation reaction in gel, or for the specific metering or proportioning of said protective antigen in biological liquids (in particular by radio immunotesting or by immuno-enzymatic tests) or in antigenic preparations.

Besides the foregoing arrangements, the invention also includes other arrangements which will be more clearly apparent from the following description.

The present invention concerns the vaccinating antigenic fraction in accordance with the foregoing arrangements, and the processes for the production thereof, the specific antibodies produced by means of said antigenic fraction, the vaccines, diagnostic agents and reagents produced by means of said vaccinating antigenic fraction, and the means suited to carrying out the processes referred to above and preparation of said antigenic fractions and said specific antibodies.

DESCRIPTION OF PREFERRED EMBODIMENTS

Figure 1:
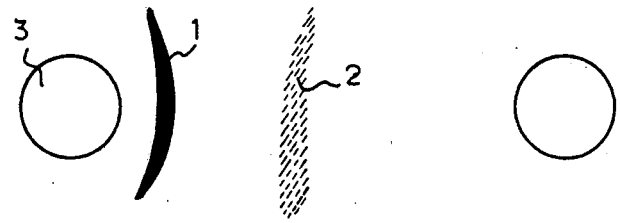
FIG. 1 shows the precipitation characteristics of an example of the present invention upon double immunodiffusion in gelose.

The invention will be better appreciated by means of the following description which includes examples of the preparation of the antigenic fraction according to the invention, examples of characterization of said antigenic fraction, examples of preparing vaccines by means of said antigenic fraction and accounts of experiments relating to vaccinations carried out on mice by means of the antigenic fraction according to the invention.

It will be appreciated however that these examples and accounts are given solely by way of illustration of the subject of the invention, in respect of which they do not in any way constitute a limitation.

EXAMPLE 1

EXTRACTION AND PURIFICATION OF A SURFACE ANTIGENIC FRACTION FROM A CULTURE OF KLEBSIELLA PNEUMONIAE SEROTYPE 2

1.—Extraction of the bacteria

The bacterial deposit of a culture of Klebsiella pneumoniae is dissolved with 60 ml of buffer LEA per gram (wet weight) of deposit.

| Buffer LEA: | | |
|---|---|---|
| lithium acetate | | 0.2 M |
| EDTA | | 10 mM |
| acetic acid QSP | → | pH-value 6 |
| sodium azide | | 0.02% |

The mixture is subjected to vigorous agitation with glass beads for a period of 2 hours at 45° C. and then centrifuged at 25 000 g for a period of 20 minutes.

A supernatant is collected: $SC_1$ (surface constituents$_1$) which is put aside.

The centrifugation deposit is dissolved in buffer LEA of the same composition as above, and a fresh extraction operation is carried out, under the same conditions as the first extraction step.

Centrifuging at 25 000 g for 20 minutes gives a deposit which is rejected, and a supernatant $SC_2$ (surface constituent$_2$).

The two supernatants $SC_1 + SC_2$ are filtered on a $0.2\mu$ Millipore filter, and a filtrate is collected, which comprises CSC or crude surface constituents.

2.—Purification of the antigen (a) The CSC is subjected to ultra-filtration on an Amicon PM 10 filter is concentrate from 10 to 30 times and produce a purified residue of surface constituents SC of which the particles with a molecular weight of less than 10 000 are rejected, so as to retain only those with a molecular weight of more than 10 000.

(b) Treatment with sodium deoxycholate (DOC)

The pH-value of SC>10 000 is adjusted to 8 with buffer TRIS.

Treatment is effected with a 5% solution of DOC in buffer TE comprising the following composition:

| Tris HCl | 10 mM |
|---|---|
| EDTA | 10 mM |
| pH-value | 8 |

The concentration of the solution of SC>10 000 is adjusted to 1% (weight/volume) of DOC (clarification of the suspension is to be observed).

This is left 30 minutes at the temperature of the laboratory, whereafter SC.DOC is collected.

(c) Precipitation with ethanol

The SC.DOC is precipitated with 4 to 5 volumes of absolute ethanol at 4° C.

Centrifuging at 40 000 g is effected, for a period of 15 minutes.

The supernatant is rejected, and the deposit is collected, and dissolved in some buffer TE to which 2% of DOC is added.

A precipitate of SC.DOC from ethanol is obtained.

(d) Passage over DEAE-cellulose

The precipitate of SC.DOC from ethanol is dialyzed against the buffer:

| Tris HCl | 10 mM |
|---|---|
| pH-value | 8 | which served to balance the cellulose, then elution is effected, increasing the molarity of the buffer Tris.

For example, for preparations of Klebsiella pneumoniae, of 0.01 M, contaminating proteins are eluted, and, at 0.5 M, the protective antigen is eluted.

(e) Calibration of the tubes containing the protective antigen by:

Protection test and/or { immunodiffusion test
immunoelectrophoresis test

The positive tubes, that is to say, those which give a 'clear' precipitation line are brought together, and concentration on an Amicon PM 10 filter is effected.

The fraction of surface constituents (SC) which is finally collected, SC peak DEAE, corresponds to the peak obtained by chromatography on DEAE-cellulose, and its composition is as follows, for Klebsiella pneumoniae serotype 2:

| | |
|---|---|
| proteins (Folin determination): | 800 γ/ml |
| neutral hexoses: | 1900 γ/ml |
| uronic acids: | 400 γ/ml |
| phosphorus: | 13 γ/ml |
| N-acetylglucosamine (traces): | 10 γ/ml |

3. Characterization of the antigenic fraction produced:

A.—In immunodiffusion in gelose

This test is carried out using gelose which is disposed in a case or box in which two wells are made: one contains the antigenic fraction of Klebsiella pneumoniae serotype 2 prepared as described above, while the other contains a immune-serum specific of the antigenic fraction.

1.—Preparation of the immune-serum

Rabbits are given a first injection of the vaccinating fraction intradermally with the complete Freund additive (doses of 100 to 1000 μg of proteins per rabbit). Boosters are injected intramuscularly, at spacings of 2 to 3 weeks, with doses of vaccinating fraction varying from 10 to 100 μg of proteins per rabbit.

Blood is taken 10 to 15 days after the boosters and the serums obtained are checked, by double immunodiffusion in gelose. The rabbits are slaughtered when the levels of antibodies produced are satisfactory (after 2 to 4 boosters).

2.—By double diffusion in gelose, two precipitates are obtained (as will be seen from FIG. 1 of the accompanying drawing):

(a) precipitate No. 1 has the following characteristics:
it is the first precipitate, starting from the well 3 of the antigen;
it is substantially centered on the antigen well;
it has a clear contour line;
it is common to different serotypes of Klebsiella pneumoniae;
it is suppressed if the antigenic preparation was previously treated by sodium hydroxide under the following conditions:
0.25 N NaOH for 3 hours at 56° C.;

(b) precipitate No. 2 has the following characteristics:
it is at a greater distance from well 3 of the antigen than precipitate No 1 and its position varies between the antigen and antibody wells;
its outlines are blurred;
it is inhibited by oses; if glucuronic acid (which is one of the constituents of the specific capsular polyoside (CP) of serotype 2 of Klebsiella pneumoniae) is added to the gelose which is the seat of the immunodiffusion reaction, in a proportion of 50 mg/ml of gel, precipitate No. 2 does not appear.

These two precipitates can be close to each other to a greater or lesser degree and in some cases they may be merged.

The following experiments carried out by the Applicant permitted him to show that the presence in the antigenic fraction, of determinants responsible for the formation of precipitate No. 1 is essential for the antigenic fraction to provide good protection: the protective capacity of the vaccinating antigenic fraction is essentially linked to the presence and the extent of precipitate No 1.

Experiment No. 1

Figure 2:
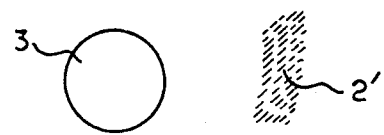
FIG. 2 shows the precipitation characteristics obtained upon immunodiffusion in gelose in accordance with experiment number 1 in the present specification.

A preparation isolated from cultures of Klebsiella pneumoniae by conventional methods (HEIDELBERGER et alia, J Exp. Med. 1950, 91, pages 341-349 for Pneumococcus; PIER et alia, Infection & Immunity 1978, 22 (3), pages 908-925 for Pseudomonas aeruginosa) makes it possible, by immunodiffusion reaction in gelose, to produce only a 'blurred' line corresponding to precipitate No. 2 which is a capsular polyoside (CP) virtually devoid of vaccinating capacity ($DP_{50}$=of the order of 80 ng): see FIG. 2, in which, in the vicinity of the antigen well containing the capsular polyose serotype 2, in the presence of anti-capsular polyoside serotype 2, there is a blurred precipitation line No 2' which is characteristic of the CP.

Experiment No. 2

Fresh preparations of capsular polyoside containing about 4% of proteins (which in this case are considered as contaminants) show a 'clear' line, in immunodiffusion. After lyophilization, there is obtained almost exclusively the 'blurred' line which gives poor vaccination (100 ng of CP=$DP_{50}$ for mouse). The results obtained hereinafter show that the $DP_{50}$ is much lower with the purified vaccinating antigenic fraction formed by the capsular polyoside part and the peptidic part, in accordance with the present invention.

The definition in vitro of the protective antigenic fraction according to the invention is as follows:

Experiment No. 3

In a box or case of gelose containing glucuronic acid (one of the components of CP), two wells are made: one contains the antigen of Klebsiella pneumoniae type 2 which is prepared in accordance with the process developed by Applicant, and the other contains a specific immune-serum of the antigen. Only one precipitation line, which is of the so-called 'clear line' nature, is observed, being of weaker intensity than in Experiment No. 2, close to the antigen well.

Experiment No. 4

The conditions are identical to those of Experiment No. 3 but the gelose does not contain glucuronic acid. Two precipitation lines are observed: one is a 'clear' line, close to the antigen well, and a second line which is more 'blurred' is disposed between the two wells.

Experiment No. 5

Markings with iodine 125, which is a specific method for revealing proteins, prove in immunodiffusion and in immunoelectrophoresis, that the 'clear' line comprises a peptidic part. With the results obtained in Experiments Nos 3 and 4 which prove the presence of capsular polyoside, it can be concluded that there is an association of 'glycopeptide' type which is responsible for the protective capacity in regard to immunization steps with mice.

It turns out from the foregoing that:

there is capsular polyoside in the vaccinating antigenic fraction according to the present invention;

another substance is associated with said polyoside;

the fact that in Experiment No. 3 the 'clear line' is weaker in intensity than in Experiment No. 4 means that determinants in the 'blurred' line are associated with the substance precipitating in the form of the 'clear line'.

It should be made clear that the vaccinating capacity is linked to the 'clear line' which disappears if the vaccinating antigen preparation is treated with sodium hydroxide under the following conditions:

0.25 N NaOH for 3 hours at 56° C.; a substantial reduction in the protective capacity is observed.

As indicated by the global composition of the purified vaccinating fraction, a protein or a peptide is certain to be present. However a treatment with "Pronase" (mixture of proteases) does not modify the characteristic appearance of the 'clear line' in immunodiffusion and the protective capacity on mice is retained.

Experimental conditions:

0.5 ml of SC peak DEAE in a proportion of 1900 $\gamma$/ml of proteins are incubated with 10$\gamma$ of "Pronase" in 0.3 ml of buffer Tris HCl with a pH-value of 7.8, for 48 hours, at a temperature of 56° C.

B.—The characterization revealed by immunodiffusion in gelose is corroborated by electrophoresis.

Figure 3:
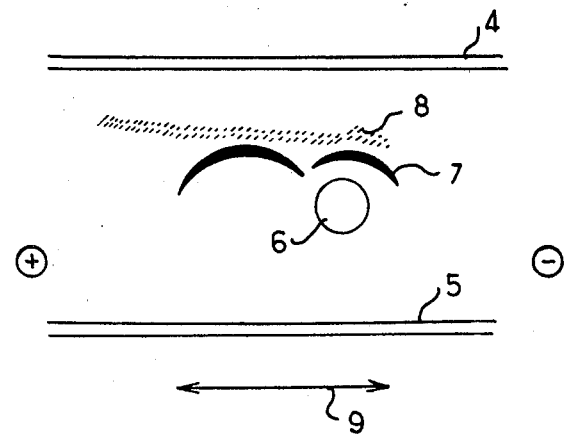
FIG. 3 shows the precipitation characteristics upon electrophoresis in gel of an example of the present invention.

In fact, electrophoresis in gel of polyacrylamide shows that the part responsible for the vaccinating capacity remains in the upper third (negative terminal) of the normal gel or the gel with SDS 2%+mercaptoethanol, at 5% (applied voltage=7.5 mA). In immunoelectrophoresis (buffer veronal, pH-value 8.6 and 5 volts/cm for two hours), there is obtained the immunologic image shown in FIG. 3 of the accompanying drawing in which:

reference 4 denotes the well of immune-serum antiserotype 2, reference 5 denotes the well immune-serum antiserotype 1, reference 6 denotes the well of the surface antigenic fraction according to the invention, extracted from Klebsiella pneumoniae type 2, reference 7 denotes the 'clear' line, reference 8 denotes the 'blurred' line, reference 9 denotes the VCM or vaccinating capability on mice.

This characterization also shows that the protective activity is due to the 'clear' precipitation line and therefore to the peptide-capsular polyoside association. The 'blurred' line is specific of the serotype.

EXAMPLE 2

EXTRACTION AND PURIFICATION OF A SURFACE ANTIGENIC FRACTION FROM KLEBSIELLA PNEUMONIAE

1.—Extraction of the bacteria

The bacterial deposit of a culture of Klebsiella pneumoniae is dissolved in 60 ml of buffer LEA per gram (wet weight) of deposit.

| Buffer LEA: | | |
|---|---|---|
| lithium acetate | | 0.2 M |
| EDTA | | 10 mM |
| acetic acid QSP | → | pH-value 6 |
| sodium azide | | 0.02% |

The mixture is subjected to vigorous agitation with glass beads for a period of two hours at 45° C. and then centrifuged at 25 000 g for 20 minutes. A supernatant $SC_1$ (surface constituents$_1$) is collected and put aside. The centrifugation deposit is dissolved in buffer LEA of the same composition as above and a fresh extraction operation is carried out under the same conditions as the first extraction step.

Centrifuging at 25 000 g for 20 minutes produces a deposit which is rejected, and a supernatant $SC_2$ (surface constituents$_2$).

The two supernatants $SC_1+SC_2$ are filtered on a 0.2 $\mu$Millipore filter, and a filtrate comprising CSC, crude surface constituents, is collected.

2.—Preparation of the immune-serum

The conditions of preparation of the immune-serum are identical to those described in Example 1 above.

In an alternative form, the antigenic fraction used for immunization may be formed:

either by preparations of surface antigens, which are purified by biochemical methods described in the literature, or by precipitate No 1 which is cut out in the gelose in situ, after washing of the gelose to remove the antigens and the antibodies which have not reacted.

3.—The antibodies contained in the immune-serum produced in 2. above are rendered insoluble by polymerization with glutaraldehyde and loaded into a column into which the crude surface constituents produced in 1. above are passed.

By affinity chromatography on such immuno-adsorbents, by purification of the fraction produced in 1. above, there is produced an antigenic fraction defined by the first peak which issues on the DEAE-cellulose column, for an absorption at 280 nm in ultra-violet, the composition of which was given hereinbefore.

The composition, after purification on an immunoadsorbent, is substantially the same as after passing over a DEAE column.

The activity of the antigenic fraction produced by this purification process is very good since it is from 0.1 to 0.3 ng (DP 50).

ACCOUNTS OF VACCINATION EXPERIMENTS ON MICE

In the experiments which are described hereinafter, use is made of the purified antigenic fraction extracted from cultures of Klebsiella pneumoniae, types 1 and 2, as produced in Example 1.

A.—Experimental procedure:

SWISS mice, four weeks old, subcutaneous immunization of 0.5 ml of product in increasing levels of dilution with apyrogenic physiological serum, 14 days after immunization, test with 100 $DL_{50}$ of the virulent strain intraperitoneally.

Tests intravenously or by aerosol give the same results as intraperitoneally:

calculation of the 50% protective dose (=DP 50) is performed in accordance with the method of Reed &

Muench (Amer. J. Hyg. 1938, 27, pages 493–497). The DP 50 is the dose which protects 50% of the mice.

B. - Results:

| Vaccinating fraction | | DP 50 |
|---|---|---|
| Klebsiella pneumoniae Type 2 | crude surface antigen (= CSC) | 10 ng of proteins |
| | SC peak DEAE (antigenic fraction according to the invention) | 1 ng of proteins |
| Klebsiella pneumoniae Type 1 | CSC | 100 ng of proteins |
| | SC peak DEAE | not done |
| Streptococcus pneumoniae Type 1 | CSC | 1.5 ng of proteins |
| | CSC treated with deoxycholate ethanol | 0.4 ng of proteins |
| Streptococcus pneumoniae Types 2 & 3 | CSC | 400 ng of proteins |
| | CSC treated with deoxycholate ethanol | not done |

It will be seen from the foregoing description that, irrespective of the methods of performance, embodiment and use adopted, the result obtained is a vaccinating glycopeptidic antigenic fraction with a very high degree of immunogenicity, which is isolated from cultures of pathogenic germs and which, in comparison with the antigenic fractions produced in accordance with the prior art, has important properties and advantages, some of which have been referred to hereinbefore and others of which will be apparent from use of said antigenic fraction.

As will be apparent from the foregoing, the invention is in no way limited to the modes of performance, embodiment and use thereof as described above in more explicit detail; on the contrary, it covers all alternative forms thereof which may occur to the mind of the man skilled in the art, without thereby departing from the scope and spirit of the present invention.

I claim:

1. A process for extracting and purifying a vaccinating antigenic fraction, comprising:
   extracting a bacterial deposit one to several times, with very vigorous agitation, by a suitable buffer with a pH-value of close to 6, said bacteria being a pathogenic germ which neither secretes nor excretes toxins, and which contains a protective antigen defined by a line of precipitation centered on the antigen well, in immunodiffusion in gelose, when opposed to an immune-serum from an animal treated by a culture of the same pathogenic germ;
   concentrating the supernatant obtained containing the crude surface constituents by ultra-filtration, collecting only the particles whose molecular weight is more than 10,000;
   treating the ultrafiltrate produced with sodium deoxycholate (DOC) in a suitable buffer with a pH-value of close to 8;
   precipitating the treated ultra-filtrate with absolute ethanol;
   dissolving the precipitate produced with the same buffer with a pH-value of close to 8 with the addition of 2% of DOC;
   dialyzing the obtained solution against the buffer Tris-HCl with a pH-value of 8; adsorbing on DEAE-cellulose;
   eluting the antigen with the same buffer used with increasing molarity; and then
concentrating by ultra-filtration.

2. A process according to claim 1, wherein said extracting step comprises extracting with a buffer comprising:

| lithium acetate | 0.2 M |
|---|---|
| EDTA | 10 mM |
| sodium azide | 0.02% |
| acetic acid QSP → | pH-value 6 | in proportion of 50 to 70 ml of buffer per gram of wet bacterial deposit.

3. A process according to claim 1, further including the step of filtering the solution of crude surface constituents on a Millipore filter before said ultra-filtration step is carried out.

4. A process according to claim 1, wherein said treating step comprises treating the ultra-filtrate, which is adjusted to a pH-value of close to 8 by the buffer Tris, with a 5% solution of DOC in buffer Tris-HCl with a pH-value of 8, formed by:

| Tris-HCl | 10 mM |
|---|---|
| EDTA | 10 mM | so as to adjust the concentration of the solution of the surface constituents to about 1% (weight/volume) of DOC.

5. A process according to claim 1, wherein said precipitating step comprises precipitating the treated ultra-filtrate by four to five times its volume of absolute alcohol.

6. A process according to claim 1, further including the step of calibrating the tubes containing the antigen after passing over a DEAE-cellulose column by the protection test and/or the immunodiffusion test and/or the immunoelectrophoresis test.

7. A process for extracting and purifying the vaccinating antigenic fraction according to claim 1 comprising producing said fraction by purification of a preparation containing said surface antigens, by affinity chromatography.

8. A process according to claim 7, wherein said purification by affinity chromatography is performed using an immunoadsorbent formed by antibodies which are specific of the component which forms the 'clear' line precipitate, which are rendered insoluble by any suitable means.

9. A process according to claim 8, wherein said specific antibodies are produced by hyperimmunization of mammals such as the rabbit in particular, by a preparation of surface antigens of pathogenic germs, in respect of which immunization is to be obtained.

10. A process according to claim 9, wherein said specific antibodies are produced by injection into an animal to be immunized of preparations of surface antigens which are purified by per se known biochemical methods.

11. A process according to claim 9 wherein said specific antibodies are produced by the direct use of the 'clear' line precipitate which is formed in the gelose in the course of the immunodiffusion reaction, which precipitate is recovered by cutting out in situ in the gelose, advantageously after washing of said gelose to remove the antigens or the antibodies which are not complexed in the course of the immunodiffusion reaction, whereafter it is injected in the animal to be immunized.

12. A process according to claim 11, wherein the clear line precipitate is produced using purified specific reagents of the determinant.

13. A process according to claim 11, wherein the clear line precipitate is produced using preparations of antigens and antibodies, which have not been purified.

14. A process according to claim 8, wherein the specific antibodies used as immunoadsorbents, in the method for purification of the antigens by affinity chromatography, are recovered after having collected the blood of the hyperimmunised animals and after having separated from the red blood corpuscles, the serum which is rich in specific antibodies.

15. A process according to claim 8, wherein the antibodies are rendered insoluble by polymerisation by means of glutaraldehyde.

16. A process according to claim 8, wherein the antibodies are rendered insoluble by fixing on beads of suitable polymers or on glass beads which are suitably activated.

17. A process according to claim 7, wherein the preparation of surface antigens which is subjected to purification by affinity chromatography is selected from the group which comprises bacteria cultures or the supernatants of such cultures, or the supernatants containing the crude surface constituent, which are produced by extraction of a bacterial deposit, or by the ultra-filtrate produced after ultra-filtration of the supernatant containing the crude surface constituent, and treatment of the latter by sodium deoxycholate (DOC).

* * * * *